United States Patent [19]

Dittmar et al.

[11] Patent Number: 4,711,775
[45] Date of Patent: Dec. 8, 1987

[54] COSMETIC COMPOSITIONS

[75] Inventors: Walter Dittmar, Hofheim; Eberhard Futterer; Gerhard Lohaus, both of Kelkheim, all of Fed. Rep. of Germany

[73] Assignee: Hoechst Aktiengesellschaft, Frankfurt am Main, Fed. Rep. of Germany

[21] Appl. No.: 677,891

[22] Filed: Dec. 4, 1984

Related U.S. Application Data

[60] Continuation of Ser. No. 478,857, Mar. 25, 1983, abandoned, which is a continuation of Ser. No. 21,948, Mar. 19, 1979, abandoned, which is a division of Ser. No. 605,210, Aug. 15, 1975, Pat. No. 4,185,106, which is a continuation of Ser. No. 377,440, Jul. 9, 1973, abandoned.

[30] Foreign Application Priority Data

Jul. 11, 1972 [DE] Fed. Rep. of Germany ....... 2234009

[51] Int. Cl.$^4$ ................................. A61K 7/06
[52] U.S. Cl. ..................... 424/70; 424/DIG. 1; 424/DIG. 2; 424/DIG. 4
[58] Field of Search ............ 424/70, DIG. 1, DIG. 4, 424/DIG. 2

[56] References Cited

U.S. PATENT DOCUMENTS

| | | | |
|---|---|---|---|
| 2,540,218 | 2/1951 | Shaw | 260/297 Z |
| 2,742,393 | 4/1956 | Bernstein et al. | 424/263 |
| 2,748,142 | 5/1956 | Clauson-Kaas et al. | 260/297 Z |
| 2,809,971 | 10/1957 | Bernstein et al. | 260/270 |
| 2,922,793 | 1/1960 | Rockett | 424/263 X |
| 3,235,455 | 2/1966 | Judge et al. | 424/263 X |
| 3,236,733 | 2/1966 | Karsten et al. | 424/263 |
| 3,269,904 | 8/1966 | Bernstein et al. | 424/263 |
| 3,583,999 | 6/1971 | D'Amico | 260/294.8 |
| 3,644,626 | 2/1972 | Witzel | 424/263 |
| 3,655,897 | 4/1972 | Witzel | 424/263 X |
| 3,883,545 | 5/1975 | Lohaus et al. | 424/263 X |
| 3,968,118 | 7/1976 | Lohaus et al. | 424/263 X |
| 3,972,888 | 8/1976 | Lohaus et al. | 260/297 Z |

FOREIGN PATENT DOCUMENTS

| | | | |
|---|---|---|---|
| 4666268 | 5/1970 | Australia | 424/263 |
| 671117 | 9/1963 | Canada | 424/263 |
| 1795270 | 12/1971 | Fed. Rep. of Germany | 424/263 |
| 2022146 | 7/1970 | France | 424/263 |
| 222120 | 8/1968 | Sweden | 424/263 |

*Primary Examiner*—Dale R. Ore
*Attorney, Agent, or Firm*—Curtis, Morris & Safford

[57] ABSTRACT

A cosmetic composition comprising a content of an 1-hydroxy-2-pyridone of the general formula

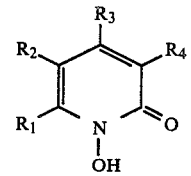

in which $R_1$ stands for hydrogen, alkyl of 1 to 17 carbon atoms, alkenyl of 2 to 17 carbon atoms, cycloalkyl of 5 to 8 carbon atoms, bicycloalkyl of 7 to 9 carbon atoms, cycloalkyl-alkyl of 1 to 4 alkyl carbon atoms, the cycloalkyl groups being optionally substituted by alkyl groups of 1 to 4 carbon atoms, aryl, aralkyl of 1 to 4 alkyl carbon atoms, aryl-alkenyl of 2 to 4 alkenyl carbon atoms, aryloxy-alkyl or arylthio-alkyl of 1 to 4 alkyl carbon atoms, benzhydryl, phenylsulfonyl-alkyl of 1 to 4 alkyl carbon atoms, furyl or furyl-alkenyl of 2 to 4 alkenyl carbon atoms, the aryl groups being optionally substituted by alkyl of 1 to 4 carbon atoms, by alkoxy of 1 to 4 carbon atoms, by nitro, cyano or halogen atoms, $R_2$ stands for hydrogen, alkyl of 1 to 4 carbon atoms, alkenyl or alkinyl of 2 to 4 carbon atoms, halogen atoms or benzyl, $R_3$ stands for hydrogen, alkyl of 1 to 4 carbon atoms or phenyl, and $R_4$ stands for hydrogen, alkyl of 1 to 4 carbon atoms, alkenyl of 2 to 4 carbon atoms, methoxy-methyl, halogen or benzyl, and/or salt thereof, which may be used as an anti-dandruff agent.

12 Claims, No Drawings

COSMETIC COMPOSITIONS

This application is a continuation of application Ser. No. 478,857 filed Mar. 25, 1983, now abandoned, which is a continuation of Ser. No. 21,948 filed Mar. 19, 1979 (now abandoned), which is a divisional of Ser. No. 605,210 filed Aug. 15, 1975 (now U.S. Pat. No. 4,185,106 granted Jan. 22, 1980), which is a continuation of application Ser. No. 377,440 filed July 9, 1973 (now abandoned).

The present invention relates to the use of 1-hydroxy-2-pyridones as anti-dandruff agents, especially of cosmetic compositions effective against dandruff, which comprise a content of 1-hydroxy-2-pyridones of the general formula

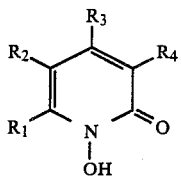

and/or the salts thereof.

In the above formula, $R_1$ stands for hydrogen, alkyl of 1 to 17 carbon atoms, alkenyl of 2 to 17 carbon atoms, cycloalkyl of 5 to 8 carbon atoms, bicycloalkyl of 7 to 9 carbon atoms, cycloalkylalkyl of 1 to 4 alkyl carbon atoms, the cycloalkyl groups being optionally substituted by alkyl groups of 1 to 4 carbon atoms, aryl, aralkyl of 1 to 4 alkyl carbon atoms, arylalkenyl of 2 to 4 alkenyl carbon atoms, aryloxy-alkyl or arylthio-alkyl of 1 to 4 alkyl carbon atoms, benzhydryl, phenylsulfonyl-alkyl of 1 to 4 alkyl carbon atoms, furyl or furylalkenyl of 2 to 4 alkenyl carbon atoms, all the aryl groups mentioned being optionally substituted by alkyl of 1 to 4 carbon atoms, by alkoxy of 1 to 4 carbon atoms, by nitro, cyano or halogen, $R_2$ stands for hydrogen, alkyl of 1 to 4 carbon atoms, alkenyl or alkinyl of 2 to 4 carbon atoms, halogen or benzyl, $R_3$ stands for hydrogen, alkyl of 1 to 4 carbon atoms or phenyl, and $R_4$ stands for hydrogen, alkyl of 1 to 4 carbon atoms, alkenyl of 2 to 4 carbon atoms, methoxymethyl, halogen or benzyl.

In the compounds of the above formula to be used as anti-dandruff agents according to the invention, the individual substituents within the scope of the above-cited definitions may have the following meanings:

$R_1$ may stand for hydrogen, straight or branched chain alkyl of 1 to 17 carbon atoms, preferably 1 to 11 carbon atoms, for example methyl, ethyl, propyl, i-propyl, butyl, pentyl, heptyl, octyl, 2,4,4-trimethylpentyl, undecyl, dodecyl, stearyl; alkenyl of 2 to 17, preferably of 3 to 8 carbon atoms, for example propenyl, isobutenyl, octenyl, 2,2-dibutyl-vinyl, heptadecenyl, cyclohexenylidene-methyl; cycloalkyl of 5 to 8 carbon atoms, for example cyclopentyl, cyclohexyl, cycloheptyl, cyclooctyl, preferably cyclohexyl; bicycloalkyl of 7 to 9 carbon atoms, preferably 2-bicyclo[2,2,1]heptyl; cycloalkylalkyl, the alkyl group having 1 to 4 carbon atoms, for example cyclopentyl-methyl, cyclooctyl-methyl, cyclohexyl-butyl, especially cyclohexyl-methyl, the afore-mentioned cycloalkyl groups being optionally also substituted by alkyl of 1 to 4 carbon atoms, for example methyl-cyclohexyl, dimethyl-cyclohexyl, butyl-cyclohexyl, methyl-cyclohexyl-methyl, dimethyl-cyclohexyl-propyl; aryl, for example naphthyl, especially phenyl; aralkyl having an alkyl radical of 1 to 4 carbon atoms, for example phenylethyl or phenylbutyl, preferably benzyl; arylalkenyl having an alkenyl radical of 2 to 4 carbon atoms, for example phenyl-vinyl or phenyl-butadienyl; aryloxy-alkyl having 1 to 4 alkyl carbon atoms, especially phenyloxy-methyl, or arylthio-alkyl having 1 to 4 alkyl carbon atoms, preferably phenylthio-methyl; benzhydryl, phenylsulfonyl-alkyl having 1 to 4 alkyl carbon atoms especially phenylsulfonyl-methyl; furylalkenyl having 2 to 4 alkenyl carbon atoms, for example furylvinyl. In the cited substituents, the aryl groups, especially the phenyl group, may carry one of more alkyl groups of 1 to 4 carbon atoms, preferably 1 to 2 carbon atoms, alkoxy of 1 to 4 carbon atoms, preferably methoxy; nitro, cyano or one or more halogen atoms, preferably chlorine or bromine atoms. Exemplary of such substituents are 3-methyl-phenyl, 4-methyl-phenyl, 2,4-dimethyl-phenyl, 3-methyl-4-chlorophenyl, 3,5-dichloro-phenyl, 3-bromo-4-chloro-phenyl, tert.-butyl-benzyl, 2,4-dimethyl-benzyl, 2-chloro-benzyl, 4-chloro-benzyl, 2,5-dichloro-benzyl, 4-bromo-benzyl, 3-methyl-phenoxy-methyl, 4-sec.-butyl-phenoxy-methyl, 4-bromo-phenoxy-methyl, 2,4,5-trichloro-phenoxy-methyl, 4-methyl-phenylthio-methyl, 4-chlorophenylthio-methyl, 4-methoxy-styryl, 1-(4-nitro-phenoxy)-butyl, 4-cyano-phenoxy-methyl, 4-chloro-phenyl-sulfonyl-butyl.

$R_2$ may stand for hydrogen, alkyl of 1 to 4 carbon atoms, such as propyl, butyl, especially methyl or ethyl; alkenyl or alkinyl of 2 to 4 carbon atoms, for example allyl, propargyl, halogen, for example chlorine or bromine, especially chlorine, or benzyl, $R_3$ stands for hydrogen, alkyl of 1 to 4 carbon atoms, especially methyl or ethyl, or phenyl, and $R_4$ for hydrogen, alkyl of 1 to 4 carbon atoms, especially methyl or ethyl; alkenyl of 2 to 4 carbon atoms, for example allyl; methoxy-methyl, benzyl or halogen, for example chlorine or bromine, especially chlorine.

Exemplary of substances to be used in the cosmetic compositions according to the invention as active ingredients are the following:

1-Hydroxy-2-pyridone
1-hydroxy-4-methyl-2-pyridone
1-hydroxy-6-methyl-2-pyridone
1-hydroxy-4,6-dimethyl-2-pyridone
1-hydroxy-3,4,6-trimethyl-2-pyridone
1-hydroxy-3,5,6-trimethyl-4-ethyl-2-pyridone
1-hydroxy-3-ethyl-4-methyl-6-isopropyl-2-pyridone
1-hydroxy-3,6-diethyl-4-methyl-2-pyridone
1-hydroxy-4-methyl-5-ethyl-6-butyl-2-pyridone
1-hydroxy-4-methyl-6-heptyl-2-pyridone
1-hydroxy-4-methyl-6-(1-ethyl-pentyl)-2-pyridone
1-hydroxy-4-methyl-6-(2,4,4-trimethyl-pentyl)-2-pyridone
1-hydroxy-4-methyl-6-undecyl-2-pyridone
1-hydroxy-4-methyl-6-propenyl-2-pyridone
1-hydroxy-3,4-dimethyl-6-isobutenyl-2-pyridone
1-hydroxy-4-methyl-6-octenyl-2-pyridone
1-hydroxy-4-methyl-6-(2,2-dibutyl-vinyl)-2-pyridone
1-hydroxy-3,4-dimethyl-6-heptadecenyl-2-pyridone
1-hydroxy-4-methyl-6-(cyclohexenylidene-methyl)-2-pyridone
1-hydroxy-4-methyl-6-cyclohexyl-2-pyridone
1-hydroxy-3-ethyl-4-methyl-6-cyclohexyl-2-pyridone
1-hydroxy-4-methyl-6-(methyl-cyclohexyl)-2-pyridone
1-hydroxy-3,4-dimethyl-6-(tert.-butyl-cyclohexyl)-2-pyridone 1-hydroxy-4-methyl-6-(2-bicyclo[2,2,1]heptyl)-2-pyridone
1-hydroxy-4-methyl-6-[-2-(dimethylcyclohexyl)-propyl]-2-pyridone
1-hydroxy-3,4-dimethyl-6-phenyl-2-pyridone
1-hydroxy-4-methyl-6-(4-methyl-phenyl-)-2-pyridone
1-hydroxy-4-methyl-6-(3-methyl-phenyl-)-2-pyridone
1-hydroxy-4-methyl-6-(4-tert.-butyl-phenyl)-2-pyridone
1-hydroxy-4-methyl-6-(3-methyl-4-chloro-phenyl)-2-pyridone
1-hydroxy-4-methyl-6-(3,5-dichloro-phenyl)-2-pyridone
1-hydroxy-4-methyl-6-(3-bromo-4-chloro-phenyl)-2-pyridone
1-hydroxy-4-methyl-6-(4-methoxystyryl)-2-pyridone
1-hydroxy-4-methyl-6-[1-(4-nitrophenoxy)-butyl]-2-pyridone
1-hydroxy-4-methyl-6-(4-cyanophenoxymethyl)-2-pyridone
1-hydroxy-4-methyl-6-(phenylsulfonylmethyl)-2-pyridone
1-hydroxy-4-methyl-6-[1-chlorophenylsulfonyl)-butyl]-2-pyridone
1-hydroxy-4-methyl-6-benzyl-2-pyridone
1-hydroxy-4-methyl-6-(2,4-dimethyl-benzyl)-2-pyridone
1-hydroxy-4-methyl-6-(tert.-butyl-benzyl)-2-pyridone
1-hydroxy-4-methyl-6-(2-chloro-benzyl)-2-pyridone
1-hydroxy-4-methyl-6-(4-chloro-benzyl)-2-pyridone
1-hydroxy-4-methyl-6-(2,5-dichloro-benzyl)-2-pyridone
1-hydroxy-4-methyl-6-(4-bromo-benzyl)-2-pyridone
1-hydroxy-4-methyl-6-(phenoxymethyl)-2-pyridone
1-hydroxy-4-methyl-6-(3-methylphenoxy-methyl)-2-pyridone
1-hydroxy-4-methyl-6-(4-sec.-butylphenoxy-methyl)-2-pyridone
1-hydroxy-4-methyl-6-(2,4,5-trichlorophenoxy-methyl)-2-pyridone
1-hydroxy-4-methyl-6-(4-bromophenoxy-methyl)-2-pyridone
1-hydroxy-3,4-dimethyl-6-(phenylthio-methyl)-2-pyridone
1-hydroxy-4-methyl-6-(4-chlorophenylthio-methyl)-2-pyridone
1-hydroxy-4-methyl-6-(4-methylphenylthio-methyl)-2-pyridone
1-hydroxy-3,5-dichloro-2-pyridone
1-hydroxy-4-methyl-3,5-dichloro-2-pyridone
1-hydroxy-4,6-dimethyl-3,5-dichloro-2-pyridone
1-hydroxy-3,4,6-trimethyl-5-chloro-2-pyridone
1-hydroxy-4-ethyl-5,6-dimethyl-3-chloro-2-pyridone
1-hydroxy-4-methyl-6-cyclohexyl-3,5-dichloro-2-pyridone
1-hydroxy-4-methyl-6-benzyl-3,5-dichloro-2-pyridone
1-hydroxy-4-methyl-6-phenyl-3,5-dichloro-2-pyridone
1-hydroxy-4-methyl-6-(2-naphthyl)-2-pyridone
1-hydroxy-4-methyl-6-benzhydryl-2-pyridone
1-hydroxy-4-methyl-6-furyl-2-pyridone
1-hydroxy-4-methyl-6-(furylvinyl)-2-pyridone
1-hydroxy-4-methyl-6-styryl-2-pyridone
1-hydroxy-4-methyl-6-(phenylbutadienyl)-2-pyridone
1-hydroxy-4,6-dimethyl-5-allyl-2-pyridone
1-hydroxy-4,6-dimethyl-5-benzyl-2-pyridone
1-hydroxy-4-methyl-5-propargyl-6-phenyl-2-pyridone
1-hydroxy-3-allyl-4-methyl-6-phenyl-2-pyridone
1-hydroxy-3-benzyl-4,6-dimethyl-2-pyridone
1-hydroxy-4-phenyl-6-methyl-2-pyridone
1-hydroxy-4,6-diphenyl-2-pyridone
1-hydroxy-3-methoxymethyl-4-methyl-6-(4-tolyl)-2-pyridone.

The above-cited compounds may be used both in free form and as salts. When organic bases are used, sparingly volatile bases are preferred, for example low-molecular-weight alkanolamines, such as ethanol-amine, diethanol-amine, N-ethyl-ethanolamine, N-methyl-diethanol-amine, triethanol-amine, diethylaminoethanol, 2-amino-2-methyl-n-propanol, dimethylamino-propanol, 2-amino-2-methyl-propane-diol, tri-isopropanol-amine; furthermore ethylene-diamine, hexamethylene-diamine, morpholine, piperidine, piperazine, cyclohexylamine, tributylamine, dodecylamine, N,N-dimethyl-dodecylamine, stearylamine, oleylamine, benzylamine, dibenzylamine, N-ethyl-benzylamine, dimethyl-stearylamine, N-methyl-morpholine, N-methyl-piperazine, 4-methyl-cyclohexylamine, N-hydroxyethyl-morpholine. Salts of quaternary ammonium hydroxides, for example trimethylbenzylammonium hydroxide, tetramethyl-ammonium hydroxide or tetraethyl-ammonium hydroxide may also be used, furthermore guanidine and derivatives thereof, especially the alkylated products thereof. It is, however, also possible to use, as salt-forming agents, for example low-molecular-weight alkylamines, for example methylamine, ethylamine or triethylamine. Salts with inorganic cations, for example alkali metal salts, especially sodium, potassium or ammonium salts, alkaline earth metal salts, especially magnesium or calcium salts, as well as salts with cations having 2 to 4 valencies, for example zinc, aluminium or zirconium salts, may also be used for the compounds of the invention.

The active ingredients of the above formula to be used in cosmetic compositions may, for example, be prepared according to processes as disclosed in U.S. Pat. No. 2,540,218, in German Offenlegungsschrift No. 1,795,270 or U.S. patent application Ser. No. 343,102 filed Mar. 20, 1973 now abandoned. The derivatives chlorinated in 3- and/or 5-position are advantageously obtained from the corresponding chlorine-free compounds by a subsequent chlorination reaction, for example by an action of elementary chlorine, sulfuryl chloride or hydrochloric acid in combination with an oxidizing agent, for example hydrogen peroxide. The above salts are prepared in known manner by mixing preferably equimolar amounts of salt-forming components with one another.

The said compounds to be used according to the invention are incorporated with a great variety of cosmetic compositions, especially with shampoos. Exemplary of further compositions according to the invention are the following hair care and hair dressing preparations: Hair rinses, hair conditioners, hair-restoring agents, hair tonics, wave setting lotions, hair sprays, hair dressing creams and gels, hair oils, pomades or brilliantines. These compositions are always applied to the hair or the scalp for a short or prolonged period of time, depending on their intended purpose. The addition of the compounds of the invention means a simultaneous treatment of dandruff. It is, however, also possible to prepare compositions which, above all or exclusively, serve the purpose of removing dandruff.

When the anti-dandruff agents of the invention are offered as shampoos, these may be available as transparent liquids, opaque liquids (having a pearl lustre effect), as creams, gels or even as powders or tablets as well as pressurized package. The surfactants upon which these shampoos are based may be of anionic, cationic, non ionic and amphoteric nature and may be combined with each other.

Exemplary of such anionic detergents are alkyl and alkylene carboxylates having 10 to 20 carbon atoms, alkyl ether carboxylates, fatty alcohol sulfates, fatty alcohol ether sulfates, alkylol amido-sulfates and -sulfonates, fatty acid alkylol amido-polyglycol ether sulfates, alkane sulfonates and hydroxyalkane sulfonates, olefin sulfonates, acyl esters of isoethionates, α-sulfo fatty acid esters, alkyl-benzene sulfonates, alkylphenol glycol ether sulfonates, sulfo-succinates, sulfosuccinic acid half- and di-esters, fatty alcohol ether phosphates, protein-fatty acid condensation products, alkyl monoglyceride sulfates and -sulfonates, alkyl-glyceride ether sulfonates, fatty acid methyl taurides, fatty acid sarcosinates, sulfo-ricinoleates. These compounds and mixtures thereof are used in the form of their water-soluble or water-dispersible salts, for example the sodium, potassium, magnesium, ammonium, mono-, di- and triethanol-ammonium salts and analogous alkylol ammonium salts.

Suitable cationic surface-active agents are, for example, quaternary ammonium salts, such as dialkyl-dimethyl-ammonium, chloride or bromide having 10 to 24, preferably 12 to 18 carbon atoms in the alkyl portion, alkyl-dimethyl-ethylammonium chloride or bromide of 10 to 24 alkyl carbon atoms, alkyl-trimethyl-ammonium chloride or bromide of 10 to 24 alkyl carbon atoms, preferably cetyl-trimethyl ammonium chloride or bromide, alkyl-trimethyl ammonium chloride or bromide of 20 to 22 alkyl carbon atoms, alkyl-dimethyl-benzyl ammonium chloride or bromide having 10 to 24, preferably 12 to 18, carbon atoms in the alkyl portion, N-alkyl-pyridinium chloride or bromide of 10 to 18 alkyl carbon atoms, preferably 12 to 16 carbon atoms, N—(C 10-18 alkyl)-isoquinolinium chloride, bromide or monoalkyl-sulfate, N—(alkyloyl-colaminoformylmethyl)-pyridinium chloride of 12 to 18 alkyl carbon atoms, N—(C 12-C 18 alkyl)-N-methyl-morpholinium chloride, bromide or monoalkyl sulfate; N—(C 12-C 18 alkyl)-N-ethyl-morpholinium chloride, bromide or monoalkyl sulfate, alkyl-pentaoxethylammonium chloride of 16 to 18 alkyl carbon atoms, diisobutylphenoxy-ethoxy-ethyl-dimethyl-benzylammonium chloride, salts of N,N-diethylamino-ethyl-stearyl amide and oleyl-amide with hydrochloric acid, acetic acid, lactic acid, citric acid, phosphoric acid, N-acylamido-ethyl-N,N-diethyl-N-methylammonium chloride, bromide or monoalkyl sulfate and N-acylamidoethyl-N,N-diethyl-N-benzyl-ammonium chloride, bromide or monoalkyl sulfate, acyl being preferably stearyl or oleyl.

As non ionic surface-active agents which may be used as detergents, there are for example mentioned fatty alcohol ethoxylates (alkyl-polyethylene glycols), alkylphenol-polyethylene glycols, alkylthio-polyethylene glycols, fatty amine ethoxylates (alkylamino-polyethylene glycols), fatty acid ethoxylates (acylpolyethylene glycols), polypropylene glycol ethoxylates (Pluronic (Registered Trademark)), fatty acid alkylol amides (fatty acid amido polyethylene glycols), saccharose esters, sorbitol esters, and polyglycol ether.

Exemplary of amphoteric surface-active agents to be added to the shampoos are N-alkyl-β-aminopropionates of 12 to 18 alkyl carbon atoms and N-alkyl-β-iminodipropionates of 12 to 18 alkyl carbon atoms as alkali metal salts and mono-, di- and trialkylol-ammonium salts, N-acylamido-alkyl-N,N-dimethylacetobetaine, preferably N-acyl-amidopropyl-N,N-dimethylacetobetaine of 8 to 18 acyl carbon atoms, alkyl-dimethylsulfopropyl-betaine of 12 to 18 alkyl carbon atoms, amphoteric surfactants on the imidazoline basis (Trade marks: Miranol Steinapon), preferably the sodium salt of 1-(β-carboxy-methyloxethyl)-1-(carboxymethyl)-2-lauryl-imidazolinium; amine oxides, for example alkyl-dimethyl-amine oxide of 12 to 18 alkyl carbon atoms, fatty acid amidoalkyl-dimethylamine oxide.

The compositions of the invention may, furthermore, contain further adjuvants and additives used for cosmetics, for example perfumes, dyes and colors, even those which dye or tint the hair, solvents, opacifying agents and pearl-lustre agents, for example esters of fatty acids with polyols, magnesium and zinc salts of fatty acids, dispersions on copolymer basis, thickeners, such as sodium, potassium, ammonium chloride, sodium sulfate, fatty acid alkylol amides, cellulose derivatives, natural gums, furthermore vegetable extracts, protein derivatives, such as gelatin, collagene hydrolysates, polypeptides on natural and synthetic basis, yolk, lecithin, lanolin and lanolin derivatives, fats, oils, fatty alcohols, silicones, deodorizing substances, antimicrobial agents, anti-seborrheic agents and substances which have a keratolytic and keratoplastic effect, for example sulfur, salicylic acid, and enzymes.

The shampoos are prepared in known manner by mixing the individual components and, where required, processing the mixture so as to comply with the composition intended. Some of these various forms of compositions possible are disclosed in the Examples.

Further hair cosmetics, in which the 1-hydroxy-2-pyridones of the invention may be used, are for example hair rinses, hair conditioning and hair-restoring agents, that are rinsed off the hair after some time or may remain on the hair depending on the formulation. These compositions contain, inter alia, substances selected from the group of the above-mentioned cationic surface-active agents which have brightening-up and antistatic properties on the hair.

The anti-dandruff compositions according to the invention may also be offered in the form of aqueous and aqueous-alcoholic hair tonics, wave setting lotions (hair setting lotions), gels and hair sprays as well as in the form of hair care and hair dressing creams and gels. As alcohols, ethanol and isopropanol are preferably used.

Exemplary of resins having a hair setting and hair holding effect and being incorporated in the corresponding compositions (hair setting lotions, hair sprays) in a concentration of 0.5 to 6% by weight, preferably of 1 to 3% by weight, are shellac and derivatives thereof, reaction products of colophonium with acrylic acid, poly-N-vinyl-pyrrolidone and alkylated poly-N-vinyl-pyrrolidone, poly-N-vinyl-N-alkylacetamide, polyvinyl acetate and partially hydrolyzed polyvinyl acetate, polyvinyl alcohol, alkyl esters of acrylic acid, copolymers of vinyl acetate and N-vinyl-N-alkyl-acetamide, copolymers of vinyl acetate and N-vinyl-pyrrolidone, reaction products of copolymers of vinyl acetate and acrylic acid or crotonic acid with organic bases, copolymers of vinyl acetate and maleic acid mono-esters, copolymers of vinyl acetate, vinyl pivalate and crotonic acid, copolymers of fatty acid vinyl esters and (meth)acrylic acid copolymers of (meth)acrylic esters and N-vinyl-pyrrolidone, copolymers of acrylic esters and (meth)acrylic acid, alkyl esters of copolymers of methylvinyl ether and maleic acid anhydride, alkyl esters of copolymers of olefins and maleic acid anhydride, polyvinyl acetals and polyvinyl butyrals, dimethyl-hyantoin-formaldehyde condensates, cyclohexanone-formaldehyde resins, phthalate resins, protein hydrolysates and protein derivatives, starch and cellulose derivatives which may also coontain cationic groups, as well as further film-forming agents having quaternary groups, such as reaction products of copolymers of alkyl-(meth-)acrylates and dimethyl-aminoethyl-(meth)acrylate with alkylating agents, furthermore quaternary copolymers of N-vinyl-pyrrolidone and dialkyl-amino-alkyl-(meth)acrylates.

It is furthermore possible to incorporate the compounds to be used according to the invention into anhydrous oily compositions such as hair oil, hair pomade or hair brilliantine.

All these compositions are also prepared—as already mentioned for shampoos—in known manner while adding the active ingredient used according to the invention. The anti-dandruff compositions of the invention may contain one or more of the aforementioned 1-hydroxy-2-pyridones in combination.

The anti-dandruff agent is incorporated into the compositions of the invention generally in an amount of from about 0.05 to about 10%, the concentration of special compositions within this range depending on their intended purpose. Certain compositions, for example in concentrated form, which have to be diluted prior to their use, may also have substantially higher concentrations.

In the case of compositions which are to remain on the hair, for example hair tonics, hair setting lotions, creams and the like, the concentration chosen will be lower, for example from about 0.05 to about 1%, preferably from 0.1 to 0.5%. Higher concentrations will suitably be chosen, when the cosmetic compositions, where required after dilution, have to act on the hair and the scalp for only a short time, for example shampoos and hair rinses. In this case, concentrations of from about 0.2 to about 10%, preferably about 0.5 to about 2%, may be advantageous.

It is known that 1-hydroxy-2-pyridine-thiones and the salts thereof, especially the zinc salt, are effective against dandruff. It was unexpected that the sulfur-free compounds also have an excellent anti-dandruff effect according to the invention.

Compared to the state of the art as mentioned, the utility of the 1-hydroxy-2-pyridones according to the invention has numerous advantages. In comparison to the zinc salt of 1-hydroxy-2-pyridine-thione, a superior anti-dandruff efficacy could be observed using a known test method (half-side washing of the hair is repeated over several weeks at determined intervals, each side with the two products to be compared). Whilst dandruff still showed in many cases after the standardized washing with the comparative product, the 1-hydroxy-2-pyridones used according to the invention generally removed the dandruff entirely.

An unexpected great superiority is shown by the compounds used according to the invention as to their toxicity compared to the zinc salt of 1-hydroxy-2-pyridine-thione, the best prior art anti-dandruff agent, as results from the following comparison of the $LD_{50}$-values.

$LD_{50}$, acute, p.o. rat
administered in a 0.5% tylose mucilage
a=ethanolamine salt of 1-hydroxy-4,6-dimethyl-2-pyridone
b=zinc salt of 1-hydroxy-4,6-dimethyl-2-pyridone
c=zinc salt of 1-hydroxy-4-methyl-6-(2,4,4-trimethyl-pentyl)-2-pyridone
d=ethanolamine salt of 1-hydroxy-4-methyl-6-cyclohexyl-2-pyridone, administered in starch mucilage
e=zinc salt of 1-hydroxy-4-methyl-6-cyclohexyl-2-pyridone and
f=zinc salt of 1-hydroxy-4-methyl-6-benzyl-2-pyridone.
g=zinc salt of 1-hydroxy-2-pyridine-thione

| Compound | $LD_{50}$ mg/kg) |
|---|---|
| a | more than 4480 |
| b | more than 6400 |
| c | more than 6400 |
| d | 5500 |
| e | more than 6400 |
| f | 2700 |
| g | 700 |

The above Table shows that the $LD_{50}$-values of the compounds of the invention are by far superior to the corresponding toxicity value of the known compound (g).

The compounds used according to the invention moreover have decisive and unexpected advantages regarding the possibilities of being processed into cosmetic compositions, the elegant appearance of the cosmetic and the appeal of the finished products to the consumer.

Up to the present, the zinc salt of 1-hydroxy-2-pyridine-thione has only been used in the form of suspensions for cosmetic compositions, owing to its very limited solubility in water. Such a composition necessarily requires previous grinding and preparing a dispersion of the anti-dandruff agent which is stable upon storage while having to take coresponding precautions against toxicity risks from handling the pulverulent product. The incorporation of the substance in the form of a micro-fine powder moreover involves difficulties in uniformly distributing the active ingredient in the finished composition, especially since its viscosity must not be inferior to a certain level in order to prevent the dispersed phase from settling later on. For this reason, viscosity has also to be limited when the known product is processed in the form of an aqueous dispersion. Moreover, when a powder is used, there is the risk of incorporating air and hence of an undesired formation of bubbles and foam, unless special conditions, such as reduced pressure, are additionally observed. Being limited to the two-phase system of solid/liquid also means that it has as yet not been possible at all to produce transparent and therefore cosmetically attractive compositions containing the known active ingredient, for example hair dressing gels and transparent shampoos, nor to produce transparent solutions, for example hair tonics or wave setting lotions. Neither has it been possible to produce compositions in an aerosol form owing to the risk of settling and clogging of the valve and the dispensing orifice of the nozzle or button.

In contradistinction thereto, the compounds used according to the invention can be processed without difficulties in water, alcohols and aqueous-alcoholic solutions owing to their good solubility. Due to the fact that solutions, instead of hitherto usual suspensions, can be obtained, transparent compositions having any degree of viscosity desired can be produced.

Recent examinations have shown (cf. for example, J. Soc. Cosmet. Chem. 23 (1972), pages 99 to 114) that the zinc salt of 1-hydroxy-2-pyridine-thione affords aqueous solutions and hence transparent cosmetic compositions only by an additional measure, that is by complexation with certain organic amines. Apart from additional expense in labor material, such compositions have considerable disadvantages. One is that the water content must not, in many cases, exceed a determined level, since more water adds the risk of the composition becoming cloudy due to the liberated zinc salt from the complex compound. In all the compositions on the basis of the mentioned complex compounds with organic amines, the pH-value has always to exceed 7.5, generally even 8.8, to prevent precipitation. For this reason, it has not been possible to produce weakly acid compositions, for example hair rinses having acid additives, which would comply with the pH-value of the skin and the hair. Another disadvantage is to have to avoid the presence of sodium ions in order to exclude a hydrolysis yielding sodium-1-hydroxy-2-pyridine-thione which, due to its considerable dermal toxicity, is not suitable for use in cosmetics and dermatologic compositions for topical application to the skin (cf. J. Soc. Cosmet. Chem. 23 (1972), pages 100, 112). Hence, this requirement also excludes the use of inexpensive sodium salts of anionic detergents as preferably used for the production of shampoos.

The compounds used according to the invention do, however, not have these considerable disadvantages.

As regards their stability, the compounds used according to the invention also have unexpected advantages over 1-hydroxy-2-pyridine-thiones.

For example, 1-hydroxy-2-pyridine-thione itself is sensitive to heat and not stable to light, the water-soluble salts thereof, for example the sodium salt, is moreover not stable to hydrolysis. Further, 1-hydroxy-2-pyridine-thione and the water-soluble salts thereof as well as the zinc salt which is sparingly soluble in water are sensitive to oxidation. Even mild oxidizing agents cause a formation of 2,2'-dithio-bis(pyridine-1-oxide) which may further be oxidized via the mono- and di-sulfoxide steps to yield the sulfonic acid derivatives.

In contradistinction thereto, the compounds used according to the invention are not sensitive to heat, are stable to light and resistant to hydrolysis both in the dry and dissolved state. A change by oxidation is only brought about under extreme conditions.

An unpleasant odor due to the sulfur content, which may occur upon decomposition of the prior art compounds, is missing with the substances used according to the invention.

The following Examples serve to illustrate the invention, the amounts given are by weight unless stated otherwise.

EXAMPLE 1

| Cream shampoo | |
|---|---|
| Sodium salt of the condensation product of saturated fatty acids of medium chain length and methyl taurine (of about 30% of active substance) | 70.0% |
| sodium salt of the condensation product of high-molecular-weight saturated fatty acids and methyl taurine (of about 30% of active substance) | 15.0% |
| fatty acid polyglycol ester (as opacifying agent) | 3.0% |
| sodium salt of the condensation product of saturated fatty acids of medium chain length and sarcosine (of about 65% of active substance | |
| water | 8.0% |
| ethanolamine salt of 1-hydroxy-4-methyl-6-cyclohexyl-2-pyridone | 1.0% |
| and preservatives, color and perfume | q.s. |

All the components, except perfume, preservatives, color and anti-dandruff agent were melted at 70°–75° C. The mixture was allowed to cool to about 40° C. and, while stirring, perfume, preservatives, color solution and a solution of the anti-dandruff agent in water were added. The mixture was then allowed to stand without stirring for crystallization. Instead of the above-mentioned anti-dandruff agent, the following agents were also used in the present composition: ethanolamine salt of 1-hydroxy-4-methyl-6-benzyl-2-pyridone and of 1-hydroxy-4-methyl-6-(2-bicyclo[2,2,1]heptyl)-2-pyridone, morpholine salt of 1-hydroxy-4-methyl-6-(4-chlorobenzyl)-2-pyridone and sodium salt of 1-hydroxy-3,4-dimethyl-6-(2-cyclohexylethyl)-2-pyridone. The use of the ethanolamine salt of 1-hydroxy-4-methyl-6-(2,4,4-trimethylpentyl)-2-pyridone in a 0.5% concentration has proved to be especially advantageous in the above composition.

EXAMPLE 2

| Shampoo in aerosol form | |  |
|---|---|---|
| Sodium lauryl ether sulfate (27–28% of active substance.) | 55.0% | |
| sodium lauryl sulfate (more than 90% of active substance | 5.0% | |
| coco fatty acid diethanol amide | 3.0% | |
| ethanolamine salt of 1-hydroxy-4,6-dimethyl-2-pyridone | 3.0% | |
| perfume, color and preservative | q.s. | |
| water to complete to | 100.0% | |
| charge for aerosol pack | 92% | of shampoo of the above formula |
| | 8% | of propellant mixture: dichloro-difluoro-methane(F12)/1,1,2,2-tetrafluoro-dichloro-ethane (F 114) (40:60) |

Instead of the ethanolamine salt of 1-hydroxy-4,6-dimethyl-2-pyridone, the following agents were also used in the above composition:

diethanolamine salt of 1-hydroxy-3,4,6-trimethyl-2-pyridone in a 3% concentration and triethanolamine salt of 1-hydroxy-2-pyridone in a 5% concentration, calculated on the propellant-free composition.

EXAMPLE 3

| Shampoo in tablet form | |
|---|---|
| Sodium lauryl sulfate (more than 90% of active substance) | 50.0% |
| sodium sulfate, anhydrous, sieved | 48.5% |
| magnesium stearate | 0.5% |
| ethanolamine salt of 1-hydroxy-4-methyl-6-isopropyl-2-pyridone | 1.0% |
| perfume, for example dry perfume, i.e. perfume adsorbed to magnesium carbonate, to highly disperse amorphous silicic acid or to lactose | q.s. |
| color | q.s. |

All the components were mixed in a drum to yield a homogenous powder which was then compressed into tablets.

Instead of the ethanolamine salt of 1-hydroxy-4-methyl-6-isopropyl-2-pyridone, aminopropanol salt of 1-hydroxy-3,4-dimethyl-6-propenyl-2-pyridone and ethanolamine salt of 1-hydroxy-4,6-dimethyl-3,5-dichloro-2-pyridone were also used in the above composition.

EXAMPLE 4

| Shampoo in powder form | |
|---|---|
| Sodium oleyl-methyl tauride (about 64% of active substance | 32.0% |
| sodium tripolyphosphate or sodium hexametaphosphate | 3.0% |
| sodium sulfate, anhydrous | 63.0% |
| anticaking agent, for example calcium stearate or highly disperse amorphous silicic acid or products on the basis of CaO/P$_2$O$_5$/SiO$_2$ | q.s. |
| calcium salt of 1-hydroxy-4-methyl 6-(4-tolyl)-2-pyridone | 2.0% |
| perfume, color | q.s. |

These components were mixed in a drum to yield a homogenous powder.

Instead of the calcium salt of 1-hydroxy-4-methyl-6-(4-tolyl)-2-pyridone, magnesium salt of 1-hydroxy-4-methyl-6-(3-chloro-phenyl)-2-pyridone, aluminium salt of 1-hydroxy-4-methyl-6-(2-naphthyl)-2-pyridone, tetramethyl-ammonium salt of 1-hydroxy-3-benzyl-4,6-dimethyl-2-pyridone and tetraethylammonium salt of 1-hydroxy-4,6-dimethyl-5-benzyl-2-pyridone were also used in the above composition.

EXAMPLE 5

| Transparent liquid shampoo | |
|---|---|
| on the basis of non ionic detergents coco fatty alcohol polyglycol ether with 15 ethylene oxide groups (100% of active substance) | 19.0% |
| coco fatty alcohol polyglycol ether with 10 ethylene oxide groups (100% of active substance) | 1.0% |
| coco fatty acid monoethanol amide | 1.0% |
| water | 78.0% |
| sodium salt of 1-hydroxy-4,6-dimethyl-2-pyridone | 1.0% |
| color, preservatives, perfume | q.s. |

The coco fatty alcohol polyglycol ether having 15 ethylene oxide groups and the coco fatty acid monoethanol amide were melted at 60°–70° C. At about 40° C., the mixture of coco fatty alcohol polyglycol ether having 10 ethylene oxide groups and the perfume was added and then the color solution, the preservatives and the solution of anti-dandruff agent in water were added while stirring.

EXAMPLE 6

| Shampoo (with an amphoteric surfactant) | |
|---|---|
| Sodium-lauryl polyglycol ether sulfosuccinate (about 40% of active substance) | 30.0% |
| sodium lauryl ether sulfate (27 to 28% of active substance | 10.0% |
| amphoteric surfactant on the basis of lauric acid imidazoline: sodium-1-($\beta$-carboxymethyl-oxyethyl)-1-(carboxy-methyl)-2-lauryl-2-imidazolinium | 10.0% |
| coco fatty acid monoisopropanol amide | 3.0% |
| sodium-undecylenoic acid monoethanol amido-sulfo-succinate (50% of active substance) | 4.5% |
| water | 42.0% |
| ethanolamine salt of 1-hydroxy-4-methyl-6-cyclohexyl-2-pyridone | 0.5% |
| perfume, color | q.s. |

Sodium lauryl polyglycol ether sulfo-succinate, sodium lauryl ether sulfate, amphoteric surfactant, sodium undecylenoic acid monoethanol amido-sulfo-succinate and coco fatty acid monoisopropanol amide were heated to 80° C. A solution of the color and anti-dandruff agent in water which had been heated to 60° C. was added while stirring to this solution. At 40° C. prefume was added. Another composition containing 0.2% of the ethanolamine salt of 1-hydroxy-4-methyl-6-cyclohexyl-2-pyridone and 42.3% of water was also prepared.

Instead of the ethanolamine salt of 1-hydroxy-4-methyl-6-cyclohexyl-2-pyridone, 2-amino-2-methyl-propane-diol salts of 1-hydroxy-4-methyl-6-heptyl-3,5-dichloro-2-pyridone, morpholine salt or ethanolamine salt of 1-hydroxy-4-methyl-6-phenylthio-methyl-2-pyridone, triethanolamine salt of 1-hydroxy-4,6-diphenyl-2-pyridone and dodecylamine salt of 1-hydroxy-3,4-trimethyl-5-chloro-2-pyridone were also used in the above composition.

1-Hydroxy-4-methyl-6-heptyl-3,5-dichloro-2-pyridone could be obtained as follows:

A solution of 29.7 g of sulfuryl chloride in 20 ml of methylene chloride was added dropwise within 5 minutes at room temperature to a solution of 19.9 g of 1-hydroxy-4-methyl-6-heptyl-2-pyridone in 40 ml of methylene chloride, the mixture was refluxed for 30 minutes, the solvent was distilled off and the residue was recrystallized from methanol.

Yield: 14.5 g, melting point: 87° C.

Calculated: C, 53.4%; H, 6.6%; Cl, 24.3%; N, 4.8%; found: C, 53.6%; H, 6.5%; Cl, 24.8%; N, 4.8%.

EXAMPLE 7

| Hair rinse (hair conditioner) | |
|---|---|
| Liquid lanolin, self-emulsifying | 3.0% |
| stearyl alcohol or cetyl alcohol | 2.0% |
| polyethylene glycol-400-distearate | 3.0% |
| stearyl-benzyl-dimethyl-ammonium chloride (25% of active substance or | 10.0% |
| cetyl trimethyl ammonium chloride or bromide or | 2.5% |
| alkyl-trimethyl-ammonium chloride of 20 to alkyl carbon atoms (about 80% of active substance) or | 3.0% |
| pentaoxethyl-stearyl-ammonium chloride (about 20% of active substance) | 12.5% |

| Hair rinse (hair conditioner) | |
|---|---|
| potassium salt of 1-hydroxy-4,6-dimethyl-2-pyridone | 2.5% |
| color, perfume, viscosity controlling agent, for example electrolytes, such as sodium chloride | q.s. |
| water to complete to | 100.0% |

Lanolin, fatty alcohol and polyethylene-glycol-400-distearate were melted at about 70° C. The major amount of water, in which the anti-dandruff agent had been dissolved, was also heated to about 70° C. and, while stirring, added to the oil phase. At 40° C., the remaining water with sodium chloride, color and other compounds as well as the perfume were added. The mixture was allowed to cool to 30° C. while stirring and filled into packages.

Instead of the potassium salt of 1-hydroxy-4,6-dimethyl-2-pyridone, 1% each of 1-hydroxy-4-methyl-6-(2,4,4-trimethylpentyl)-2-pyridone or of 1-hydroxy-4-methyl-6-(4-chlorophenoxymethyl)-2-pyridone were also added in the form of the ethanolamine salt. The emulsion which had been diluted with water in a ratio of 1:1 was applied to the wet hair and then rinsed off after a period of action of 5 to 10 minutes.

EXAMPLE 8

| Hair lotion | |
|---|---|
| Isopropanol or ethanol | 45.00% |
| 1-hydroxy-4-methyl-6-cyclohexyl-2-pyridone | 0.05% |
| perfume | q.s. |
| water to complete to | 100.00% |

The anti-dandruff agent was dissolved in alcohol. The perfume and then water were added to this solution. Two other compositions contained each 0.5 and 1% of the anti-dandruff agent.

Instead of 1-hydroxy-4-methyl-6-cyclohexyl-2-pyridone, the ethanolamine salt thereof as well as 2-amino-2-methyl-propanol salt and 2-amino-2-ethyl-propanol salt of 1-hydroxy-4-methyl-6-benzhydryl-2-pyridone were also added, the anti-dandruff agent having been dissolved in water and this solution being added to the alcohol combined with the perfume.

In addition, hair lotions could, for example, also contain according to the above general recipe:

Keratolytically and keratoplastically effective substances, such as sulfur and sulfur derivatives, disinfectants, such as quaternary ammonium compounds, substances which promote local blood circulation and hair growth and which reduce the loss of hair, as well as those which mainly treat the hair.

EXAMPLE 9

| Hair setting lotion | |
|---|---|
| Copolymer of 50 parts of vinyl acetate and 50 parts of N—vinyl-pyrrolidone (about 50% of active substance in isopropanol solution) | 6.0% |
| isopropanol | 40.0% |
| morpholine salt of 1-hydroxy-4-methyl-6-(4-methyl-cyclohexyl)-2-pyridone | 0.1% |
| pentaoxethyl-stearyl-ammonium chloride (about 20% of active substance) | 2.0% |
| perfume | q.s. |
| water to complete to | 100.0% |

The solution of the copolymer was diluted with the indicated amount of isopropanol. The pentaoxethyl-stearyl-ammonium chloride and the perfume and then water, in which the anti-dandruff agent had been previously dissolved, were added to this solution.

In another example, 0.5% of anti-dandruff agent were used used. Instead of the morpholine salt of 1-hydroxy-4-methyl-6-(4-methyl-cyclohexyl)-2-pyridone, N-ethyl-ethanolamine salt of 1-hydroxy-4-methyl-6-(1-ethyl-pentyl)-2-pyridone and ethanolamine salt of 1-hydroxy-4-methyl-6-(2,4-dimethyl-benzyl)-2-pyridone were also used in the above composition.

EXAMPLE 10

| Hair spray | |
|---|---|
| A mixture was prepared to yield a concentrate of the following composition: | |
| Copolymer of 90 parts of vinyl acetate and 10 parts of crotonic acid | 6.80% |
| 2-amino-2-methyl-propane-diol (for an 80% neutralization of the above copolymer | 0.59% |
| silicone oil (dimethyl-polysiloxan) having a viscosity of 20 ± 10 cSt. (at 25° C.) | 0.10% |
| lanolin (liquid, soluble in alcohols and water | 0.13% |
| 1-hydroxy-4-methyl-6-undecyl-2-pyridone | 0.08% |
| perfume | 0.10% |
| ethanol, anhydrous | 92.20% |

The concentrate was filtered and filled into spray containers at a filling ratio of
25% of concentrate to
75% of propellant (trichloro-fluoromethane (F11)/dichlorodifluoromethane (F 12) 65:35.

Instead of the ethanolamine salt of 1-hydroxy-4-methyl-6-undecyl-2-pyridone, 1-hydroxy-3,4-dimethyl-6-octenyl-2-pyridone, 1-hydroxy-4-methyl-6-stearyl-2-pyridone, 1-hydroxy-4-methyl-6-(4-methoxy-styryl)-2-pyridone and 1-hydroxy-4-methyl-6-(4-chlorophenyl-thiomethyl)-2-pyridone were used also in the above composition.

EXAMPLE 11

| Hair dressing cream | |
|---|---|
| Tertiary phosphoric ester of fatty alcohol tetraglycol ether of 12 to 14 carbon atoms | 14.30% |
| paraffin oil DAB 7, ($\eta \sim 120$ cP) | 35.70% |
| perfume | 0.30% |
| ethanolamine salt of 1-hydroxy-4-methyl-6-cyclohexyl-2-pyridone | 0.10% |
| water and preservatives | 49.60% |

The melt of emulsifier and oil was heated to 70° C. and the water phase was heated to 75° C. The water phase was added slowly while stirring to the oil phase. The perfume was added at 40° C. Instead of the ethanolamine salt of 1-hydroxy-4-methyl-6-cyclohexyl-2-pyridone, cyclohexylamine salt of 1-hydroxy-4,6-dimethyl-5-allyl-2-pyridone or N,N-dimethylstearylamine salt of 1-hydroxy-4-methyl-6-(2-furylvinyl)-2-pyridone were also used in the above composition.

EXAMPLE 12

| Hair dressing gel | |
|---|---|
| Monoethanolamine salt of mono/dilauryl-tetraglycol ether orthophosphoric ester | 13.10% |

-continued

| Hair dressing gel | |
| --- | --- |
| oleyl alcohol polyglycol ether having 5 ethylene oxide groups | 4.30% |
| oleyl alcohol | 2.90% |
| paraffin oil, (η~60 cP) | 14.60% |
| polyglycol 200 | 20.20% |
| perfume | 1.0% |
| sodium salt of 1-hydroxy-4-methyl-6-(4-methyl-cyclohexyl)-2-pyridone | 0.06% |
| water and preservatives | 43.84% |

The emulsifier-oil phase with the polyglycol was heated to 75°–80° C. and the water was separately heated to the same temperature. Prior to emulsification, the perfume was incorporated while stirring into the emulsifier-oil phase and immediately afterward the water was added while stirring. The hair dressing gel was filled in a warm state into tubes or jars.

Instead of the ethanolamine salt of 1-hydroxy-4-methyl-6-(4-methylcyclohexyl)-2-pyridone, ethanolamine salt of 1-hydroxy-4-methyl-6-(4-tolyl-thiomethyl)-2-pyridone was also used in the above composition.

We claim:

1. An anti-dandruff shampoo comprising a surfactant and, as the active anti-dandruff agent therein, from 0.2 to 10 percent of 1-hydroxy-4-methyl-6-(2,4,4-trimethylphenyl)-2-pyridone, a salt thereof, or a mixture of said pyridone with said salt.

2. A shampoo, for short-term treatment of the hair and destined to be rinsed off, comprising:
    (a) as an active ingredient, from 0.2 to 10 percent of 1-hydroxy-4-methyl-6-(2,4,4-trimethylpentyl)-2-pyridone, a salt thereof, or a mixture of said pyridone with said salt;
    (b) a surfactant; and
    (c) water or an aqueous alcoholic solution as a carrier.

3. A shampoo as in claim 2 wherein the content of (a) is from 0.2 to 2 percent.

4. A shampoo as in claim 2 wherein the surfactant is an anionic surfactant.

5. A shampoo as in claim 2 wherein the salt of the active ingredient (a) is a low molecular weight alkanolamine salt.

6. A shampoo as in claim 2 wherein the carrier (c) is water.

7. A hair rinse or hair conditioner, for short-term treatment of the hair and destined to be rinsed off, comprising:
    (a) as an active ingredient, from 0.2 to 10 percent of 1-hydroxy-4-methyl-6-(2,4,4-trimethylpentyl)-2-pyridone, a salt thereof, or a mixture of said pyridone with said salt;
    (b) a cationic surfactant; and
    (c) water or an aqueous alcoholic solution as a carrier.

8. A hair rinse or hair conditioner as in claim 7 wherein the carrier (c) is water.

9. A hair rinse or hair conditioner as in claim 7 wherein the salt of the active ingredient (a) is a low molecular weight alkanolamine salt.

10. A shampoo, for short-term treatment of the hair and destined to be rinsed off, comprising:
    (a) as an active ingredient, from 0.2 to 10 percent of 1-hydroxy-4-methyl-6-(2,4,4-trimethylpentyl)-2-pyridone, a salt thereof, or a mixture of said pyridone with said salt;
    (b) a surfactant; and
    (c) water or an aqueous alcoholic solution as a carrier, said shampoo having a physiologically acceptable pH.

11. A shampoo as in claim 10 wherein the carrier (c) is water.

12. A hair rinse or hair conditioner, for short-term treatment of the hair and destined to be rinsed off, comprising:
    (a) as an active ingredient, from 0.2 to 10 percent of 1-hydroxy-4-methyl-6-(2,4,4-trimethylpentyl)-2-pyridone, a salt thereof, or a mixture of said pyridone with said salt;
    (b) a cationic surfactant; and
    (c) water or an aqueous alcoholic solution as a carrier, said hair rinse or hair conditioner having a physiologically acceptable pH.

* * * * *